US007520248B1

(12) United States Patent
Linker

(10) Patent No.: US 7,520,248 B1
(45) Date of Patent: Apr. 21, 2009

(54) METHOD OF REMOVING AND STORING A STUN GUN DART

(75) Inventor: Carson R. Linker, Camas, WA (US)

(73) Assignee: Global Pathogen Solutions, Inc., Camas, WA (US)

( * ) Notice: Subject to any disclaimer, the term of this patent is extended or adjusted under 35 U.S.C. 154(b) by 606 days.

(21) Appl. No.: 11/269,409

(22) Filed: Nov. 8, 2005

Related U.S. Application Data

(63) Continuation-in-part of application No. 10/909,704, filed on Aug. 2, 2004, now Pat. No. 7,090,196.

(51) Int. Cl.
*A61M 5/00* (2006.01)
*B65D 83/02* (2006.01)

(52) U.S. Cl. ........................................ 119/174; 206/363

(58) Field of Classification Search ................ 119/174; 206/349, 363, 364, 365, 367; 73/167, 102, 73/501, 512, 513; 43/6; 273/108; 81/25; 604/130, 263; 473/578, 581, 585, 586; 29/263, 29/256, 264; 254/18, 19, 20, 25; 606/1
See application file for complete search history.

(56) References Cited

U.S. PATENT DOCUMENTS

| | | | | |
|---|---|---|---|---|
| 4,736,844 | A * | 4/1988 | Scott et al. | 206/370 |
| 5,642,887 | A * | 7/1997 | Orav | 473/586 |
| 5,894,925 | A * | 4/1999 | Sukiennik et al. | 206/356 |
| 6,636,412 | B2 * | 10/2003 | Smith | 361/232 |
| 2007/0039844 | A1 * | 2/2007 | Zyzelewski et al. | 206/363 |

* cited by examiner

*Primary Examiner*—Yvonne R. Abbott
(74) *Attorney, Agent, or Firm*—Timothy E. Siegel Patent Law, PLLC

(57) ABSTRACT

A method of removing a dart, having a base and a tip and wherein the base is wider than the tip, from animal soft tissue. The method makes use of a dart removal facilitating assembly, including a sharps container defining an opening sized to accept the base of the dart and also defining a slot contiguous with set opening, the slot being narrower than the base of the dart. The base of the dart is moved through the opening and the sharps container is moved so that the tip of the dart extends through the slot. Finally, the sharps container is to pull the dart out of the animal soft tissue.

7 Claims, 8 Drawing Sheets

METHOD OF REMOVING AND STORING A STUN GUN DART

RELATED APPLICATIONS

This application is a continuation-in-part of U.S. application Ser. No. 10/909,704 filed Aug. 2, 2004 now U.S. Pat. No. 7,090,196.

BACKGROUND OF THE INVENTION

The proliferation of stun guns among law enforcement, security forces and facilities for holding large animals throughout the world, has caused an unanticipated problem. Stun guns, such as the Taser® gun, work by shooting barbed darts into the subject. These darts are connected to thin wires, through which a series electric pulses is passed to pacify the subject.

After the subject has been subdued, it is necessary for a responding professional to remove the dart(s) from the subject. This is typically done by holding the subject down with one hand, while removing the dart with the other. Unfortunately, during this operation the subject may suddenly move in an effort to gain freedom. This, in turn, may throw the responding professional off balance to the point that he inadvertently jabs the barbed end of the newly removed dart into the hand used to stabilize the body part that had received the dart.

Far from being a minor, temporary injury, this brief event may have a life-long and tragically life-shortening effect on the responding professional, who may contract-hepatitis, HIV or any one out of a long list of blood born pathogens from blood on the dart. This very occurrence has become all too common, with thousands of people all infected with a deadly virus through this mechanism or a related cause, such as an intra venous needle stick. Some way must be found to make the removal of stun gun darts safer for the personnel who must remove them from the subjects.

SUMMARY OF THE INVENTION

In a first separate aspect, the present invention may take the form of a method of removing a dart, having a base and a tip and wherein the base is wider than the tip, from animal soft tissue. The method makes use of a dart removal facilitating assembly, including a sharps container defining an opening sized to accept the base of the dart and also defining a slot contiguous with set opening, the slot being narrower than the base of the dart. The base of the dart is moved through the opening and the sharps container is moved so that the tip of the dart extends through the slot. Finally, the sharps container is to pull the dart out of the animal soft tissue.

In a second separate aspect, the present invention may take the form of a dart removal facilitating assembly that comprises a sharps container defining an opening sized to accept the base of the dart and also defining a slot contiguous with the opening, the slot being narrower than the base of the dart. A handle is removeably attached to the sharps container.

The foregoing and other objectives, features and advantages of the invention will be more readily understood upon consideration of the following detailed description of the preferred embodiment(s), taken in conjunction with the accompanying drawings.

DETAILED DESCRIPTION OF THE PREFERRED EMBODIMENT(S)

Figure 1:
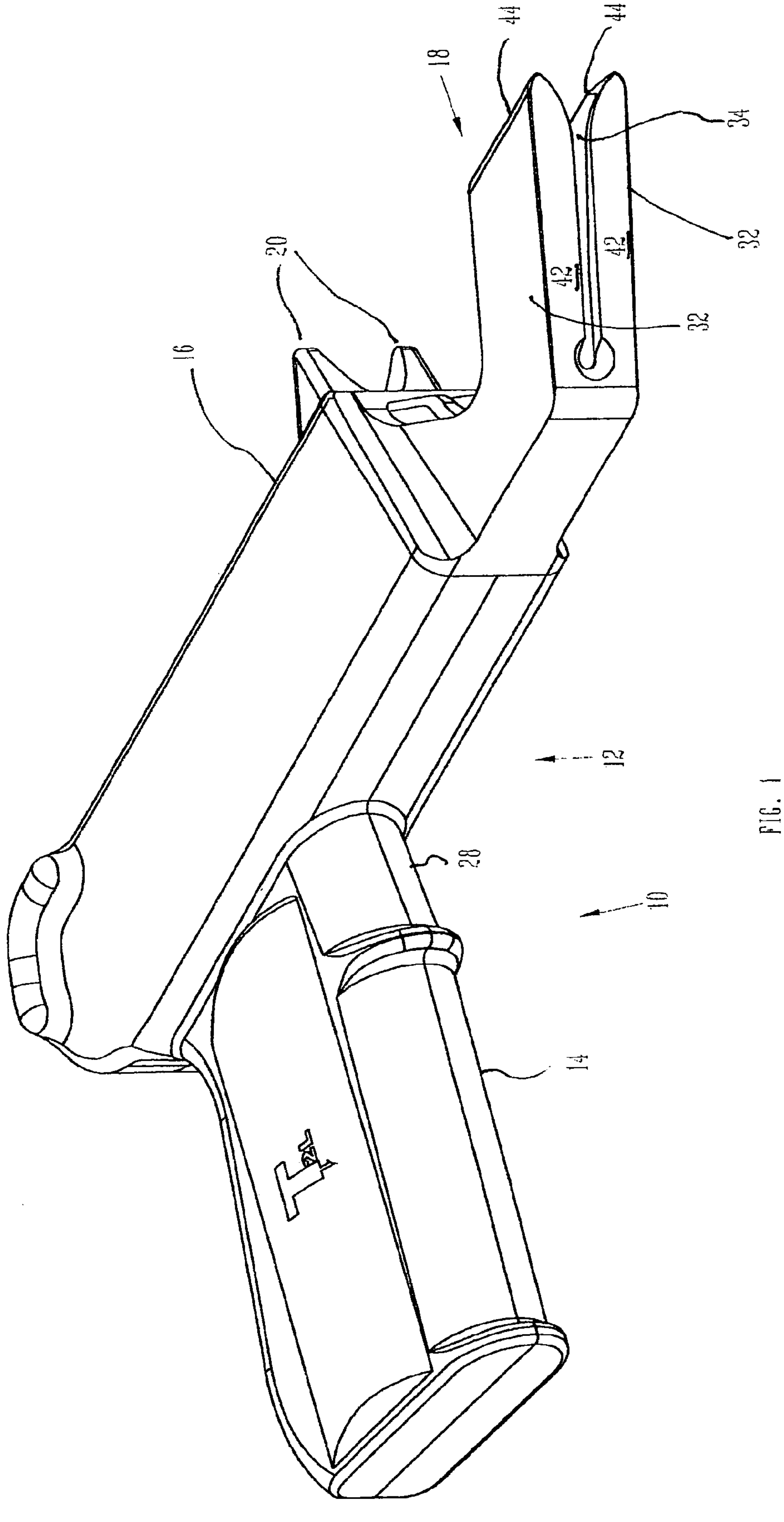
FIG. 1 is a perspective view of a dart removal tool according to the present invention.
Figure 2:
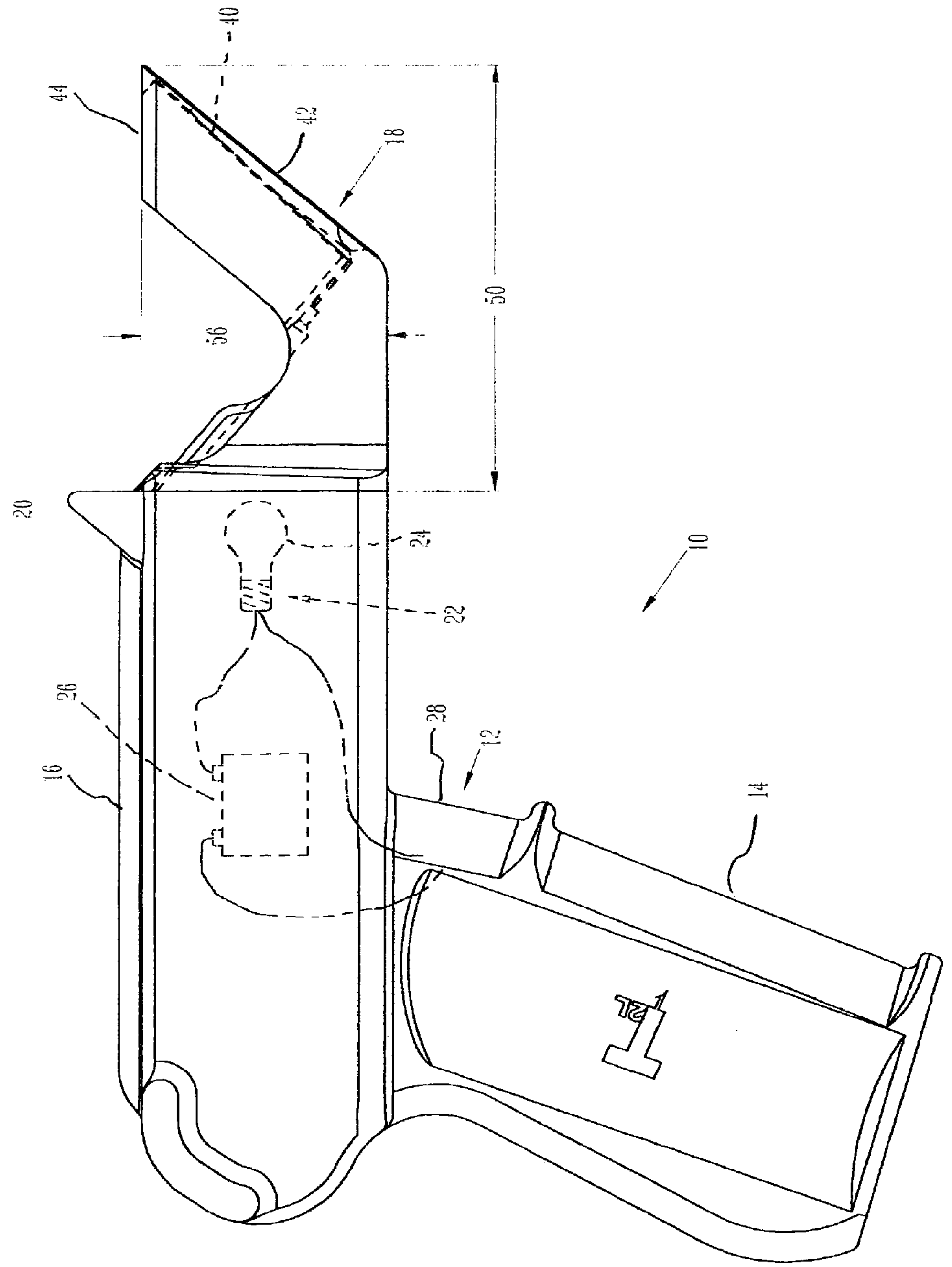
FIG. 2 is a side view of the dart removal tool of FIG. 1.

Referring to FIGS. 1 and 2, one preferred embodiment of a dart removal tool 10 according to the present invention includes handle 12, which in turn includes a hand grip 14 and a spacer 16. Detachably supported at the end of spacer 16 that is furthest from hand grip 14 is a dart removal head 18. Spacer 16 also includes a sight 20, adapted to facilitate a user in aligning tool 10 with a dart.

In addition, spacer 16 incorporates a lighting system 22 (FIG. 2), that includes a light emitting diode (LED) 24 and a battery 26. System 22 is electrically connected to and activated by a manually actuated switch 28. The end of spacer 16 that mates with head 18 is transparent, thereby permitting light from LED 24 to shine into head 18, which is made of translucent material.

Figure 3:
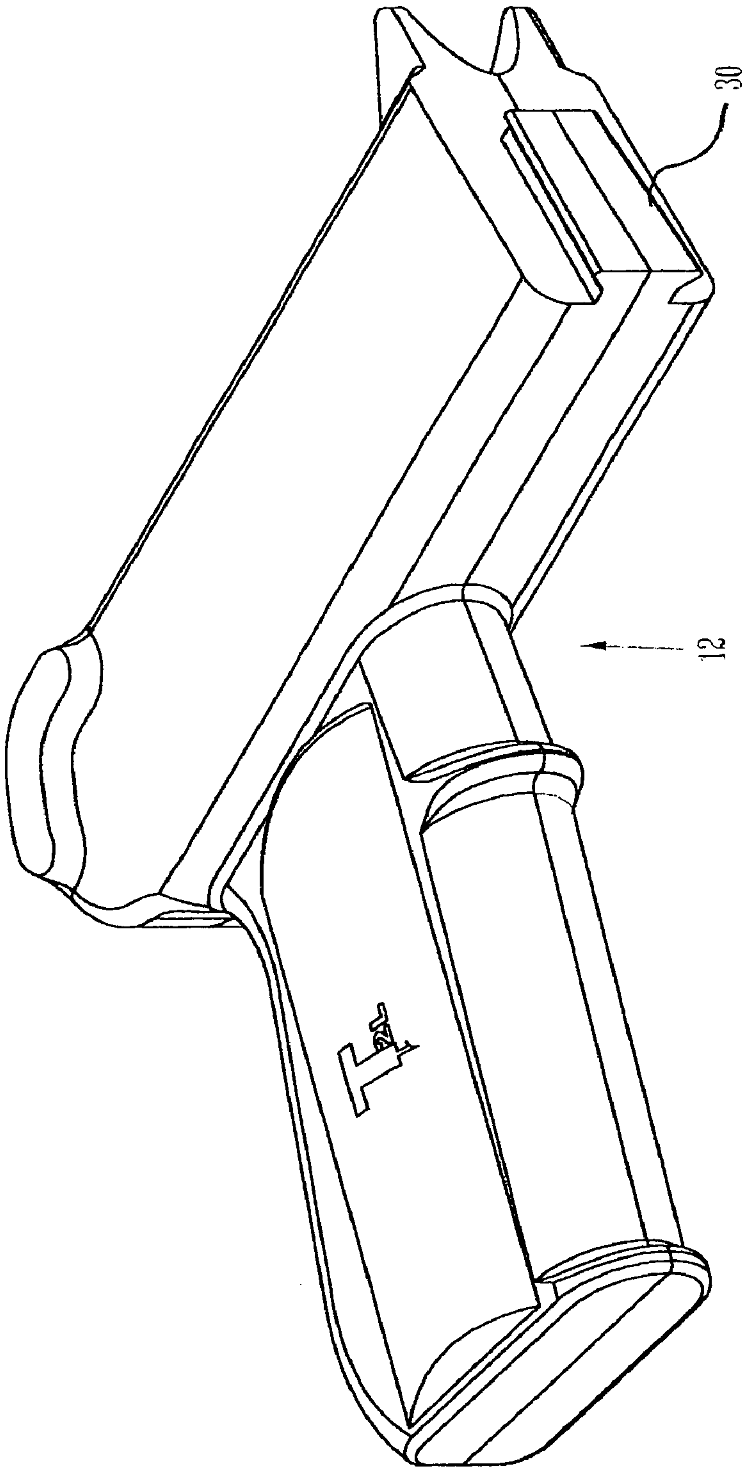
FIG. 3 is a perspective view of the handle of the dart removal tool of FIG. 1.
Figure 4:
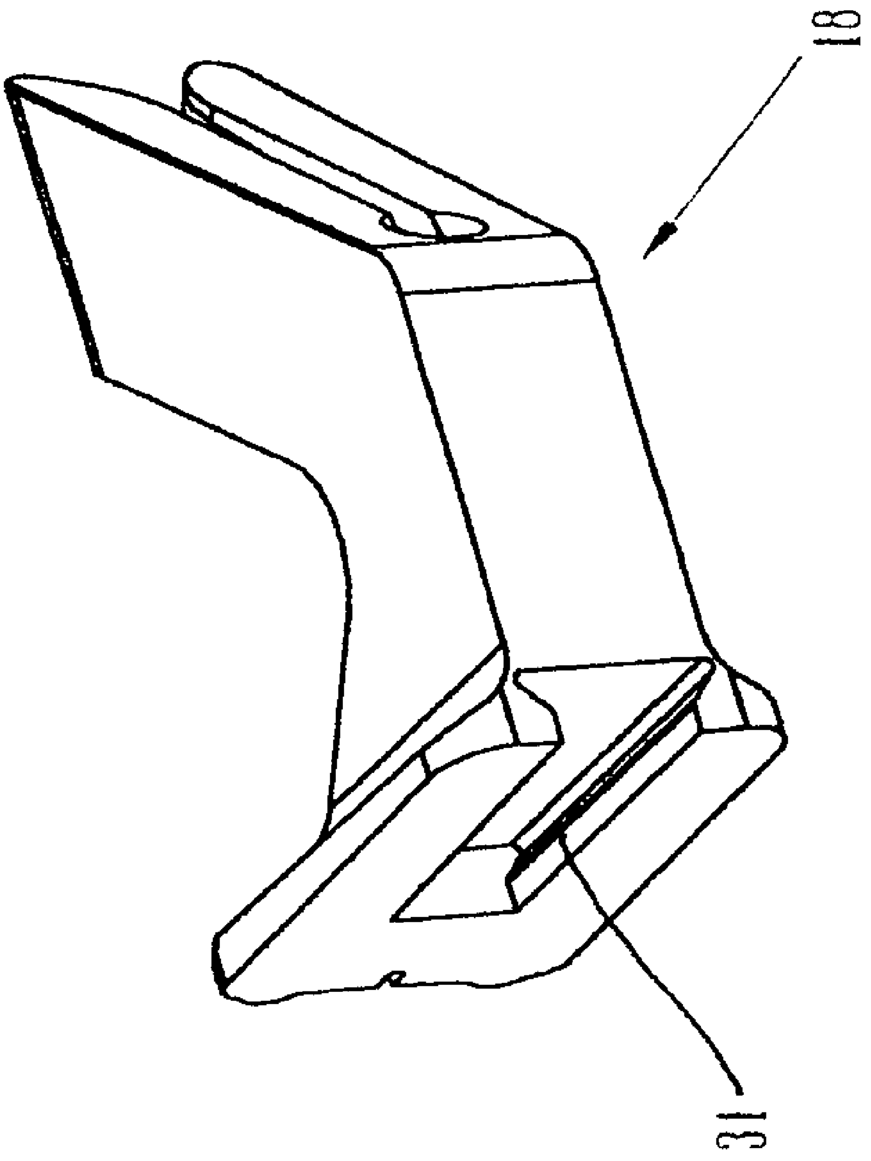
FIG. 4 is a perspective view of the head of the dart removal tool of FIG. 1.
Figure 5:
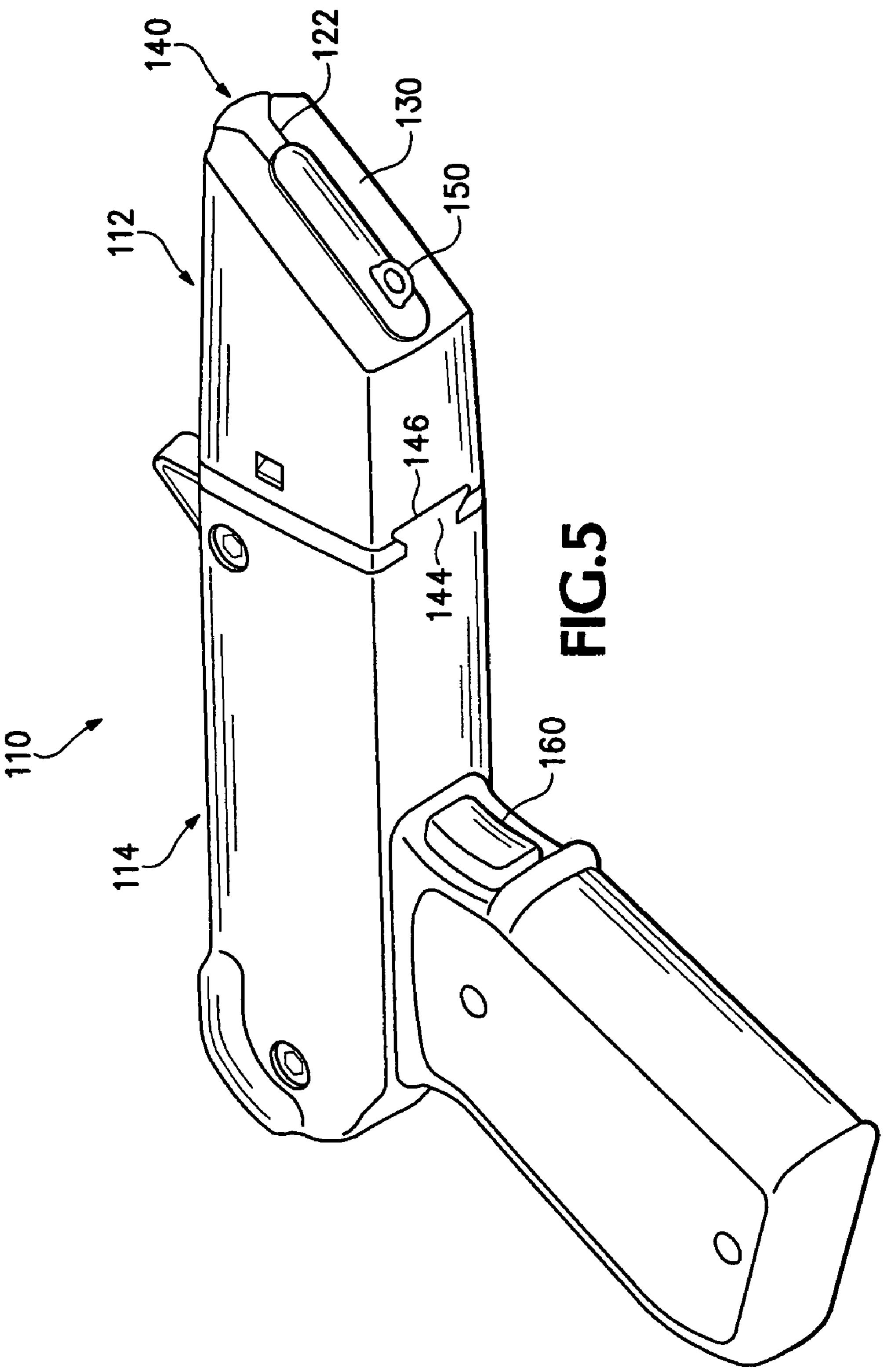
FIG. 5 is a perspective view of an alternative embodiment of a dart removal tool, having a sharps container, according to the present invention.
Figure 6:
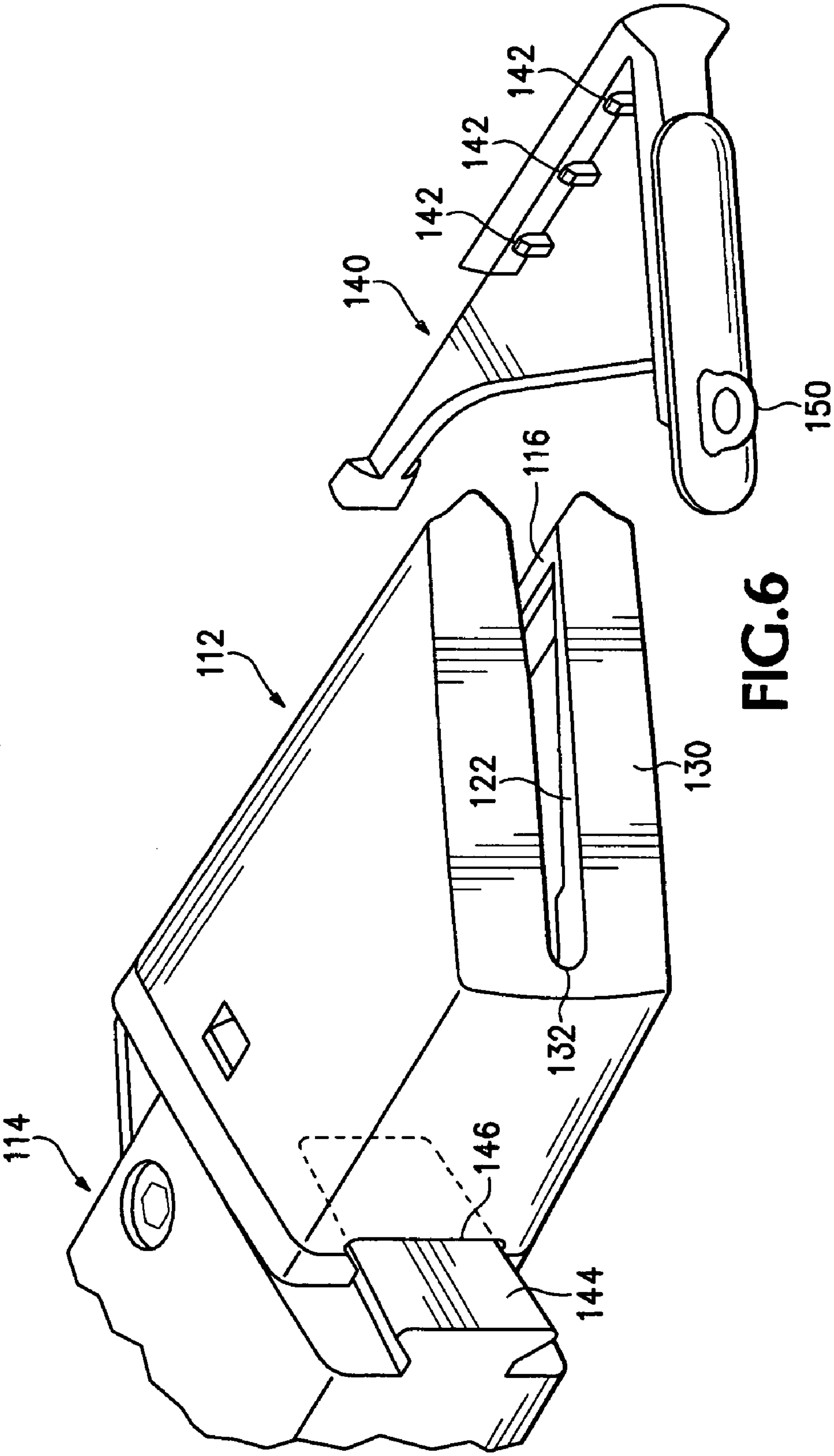
FIG. 6 is a perspective detail view of the dart removing portion of the dart removal tool of FIG. 5, in a state of partial disassembly.
Figure 7:
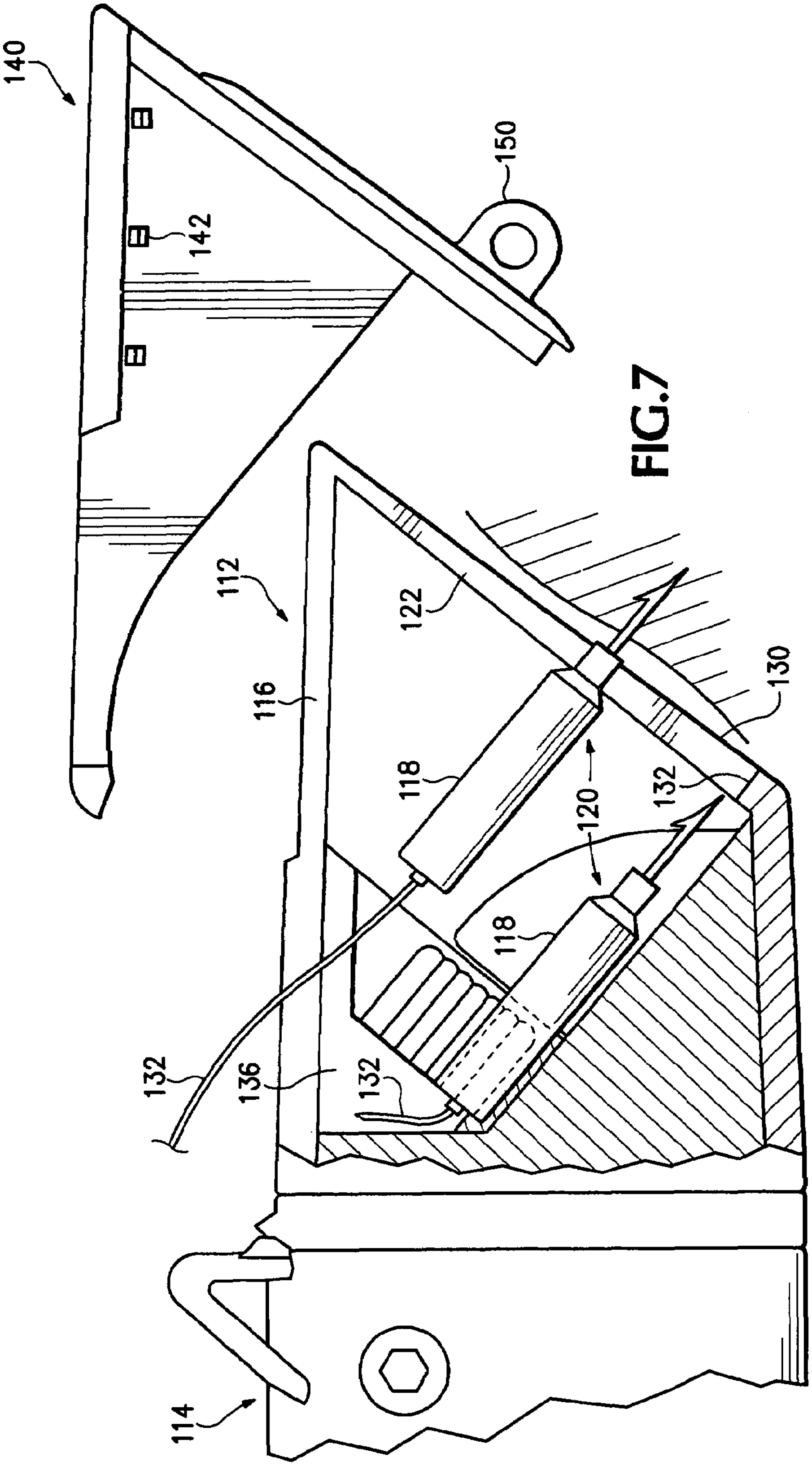
FIG. 7 is a side sectional detail view of the portion of FIG. 6, shown containing two darts and open, but with the closure near.
Figure 8:
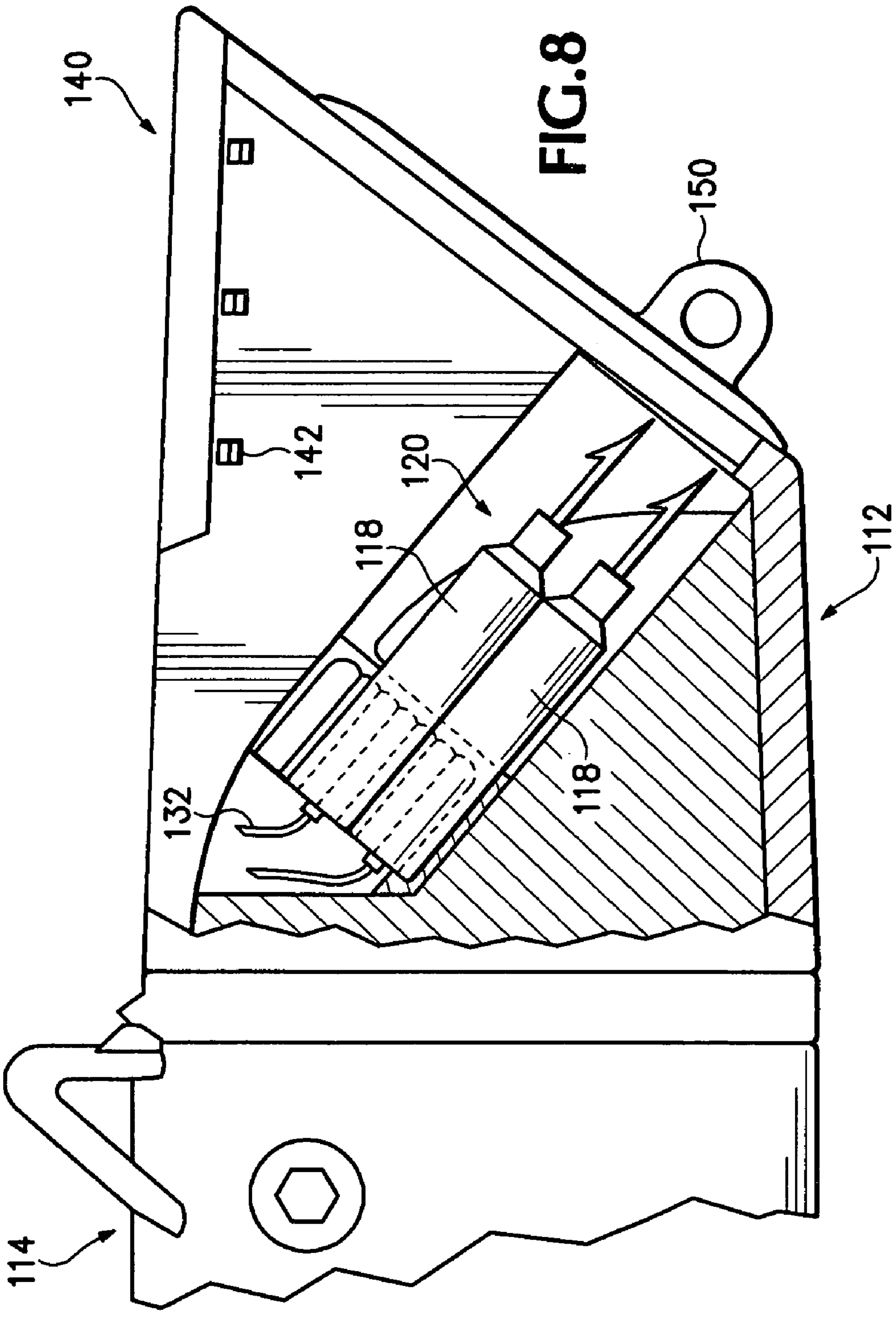
FIG. 8 is a side section detail view of the portion of FIG. 6, shown containing two darts and with the closure in place.

In greater detail, head 18 is made light weight polycarbonate material and is detachably connected to spacer 16 by a mating dovetail key 30 and groove 31 combination (FIGS. 3 and 4). A pair of ears 32 define a slot 34 (FIG. 1) adapted to engage a dart. Ears 32 and slot 34 may be considered a dart engagement portion. Referring to FIG. 2, an internal surface 40 of each ear 32, has a different slope than front surface 42, so that each ear 32 is in the form of a wedge, adapted to pull out a dart. In addition, the top surface 44 of each ear is made of roughened polymer material, thereby permitting light to escape more easily and to illuminate the area directly in front of surfaces 44.

The method of use and advantages of 10 may now be evident. A responding professional can hold tool 10 by hand grip 14 and guide it toward an embedded dart using sight 20 and the illumination provided by assembly 22. After guiding ears 32 so that dart is in slot 34, the professional may simply slide head 18 forward, so as to cause the wedge shape of each ear 32 to remove the dart. Accordingly, there is no need for the hand of the professional to touch the dart during the removal process. It is also within the scope of the method of the invention, however, for the professional to use tool 10 to restrain the part of the subject near the dart, and use his free hand to remove the dart.

Handle 14 is sized to fit comfortably in a human hand. Preferred embodiments exist with various handle sizes, to accommodate different sized hands. Spacer 16 may be of any length from 2 cm to 40 cm depending on the desired trade-off between maintaining a safe distance to the dart being removed, versus better control of the dart removal head 18. In one preferred embodiment spacer 16 has a user adjustable length. The length 50 of head 18 is preferably 7.2 cm (2.8 in) and its height 56 (FIG. 2) is preferably 4.1 cm (1.6 in).

Because tool 10 can both hold the subject down and remove the dart, it permits the responding professional to avoid using one hand to hold the subject down while the dart is removed with the other hand. As noted in the background, it is the hand used to hold the subject down that is likely to be stuck by the dart, as the dart is removed. Even if the professional does use his free hand to remove the dart, however, the hand holding tool 10 is further from the subject at the moment when the dart is removed than it would otherwise be, and is therefore safer from a chance dart puncture.

In an alternative preferred embodiment, shown in FIGS. 5-8 a dart removal tool 110 is provided that is adapted to capture a dart in a sharps container 112 that is supported on a handle 114. Sharps container 112 defines an opening 116 that is wide enough to accommodate the base portion 118 of a standard stun gun dart 120. A slot 122, which is contiguous with opening 116 is more narrow than base portion 118. Additionally, the front wall 130 increases in thickness as it progresses toward the terminus 132 of slot 122. Accordingly a tool user may orient tool 110 so that the front wall 130 is flush with the skin of a dart bearing person, move tool 110 so that dart 120 enters through opening 116. The user may then slide tool 110 along the skin so that the increasing thickness of wall 130 as it defines the sides of slot 122 pulls base portion 118 and thereby dart 120 out of the flesh of the person. This process also presses base portion 118 into a dart retaining unit 136, which is adapted to retain two darts by means of a pressure fit about base portions 118. Darts 120 may also be pulled rearward by means of wires 132 into unit 136, after which wires 132 are snipped, so that container 112 may be closed. To do this, a closure 140 may be pressed into opening 116 and slot 122, permitting resilient projections 142 to snap into place, thereby affirmatively retaining dart or darts 120 and constraining their freedom of movement within container 112.

Sharps container 112 is releasably retained on handle 114 by means of a mating dovetail 144 and dovetail key 146. Container 112 may be tagged by way of closure eye 150 and removed from the handle 114, to be placed into evidence or stored for future study. A trigger 160 actuates a light that shines through container 112, to illuminate an area about a dart 118, during use of tool 110.

In the context of this application, a human body is a type of animal body.

The terms and expressions that have been employed in the foregoing specification are used as terms of description and not of limitation. There is no intention, in the use of such terms and expressions, of excluding equivalents of the features shown and described or portions thereof, it being recognized that the scope of the invention is defined and limited only by the claims which follow.

The invention claimed is:

1. A method of removing a dart, having a base and a tip and wherein said base is wider than said tip, from animal soft tissue, comprising:

(a) providing a dart removal facilitating assembly, including a sharps container defining an opening sized to accept said base of said dart and also defining a slot contiguous with set opening, said slot being narrower than said base of said dart;

(b) accepting said base of said dart through said opening and moving said sharps container so that said tip of said dart extends through said slot; and (c) using said sharps container to pull said dart out of said animal soft tissue.

2. The method of claim 1, wherein said sharps container is increasingly thick as said slot extends from said opening and wherein said sharps container is pushed so that said increasing thickness pulls said dart out of said animal soft tissue, to pull said dart out of said soft animal tissue.

3. The method of claim 1, wherein said dart removal facilitating assembly includes a closure for said sharps container and said method further includes closing said sharp container with said closure after said dart removal, thereby affirmatively capturing said dart in said sharps container.

4. The method of claim 1, wherein said animal soft tissue is human soft tissue.

5. The method of claim 1, wherein said dart removal facilitating assembly includes a dart base accepting and retaining unit, defining a dart base shaped opening, adapted to accept and retain a base of a dart that has been slid along said slot.

6. The method of claim 1, wherein said dart removal facilitating assembly includes a handle attached to said sharps container.

7. The method of claim 6, wherein said handle is removeably attached to said sharps container.

* * * * *